(12) United States Patent
Thevasahayam

(10) Patent No.: US 10,035,124 B2
(45) Date of Patent: Jul. 31, 2018

(54) METHODS, MATERIALS, AND SYSTEMS FOR CONVERTING ALCOHOLS

(71) Applicant: EMPIRE TECHNOLOGY DEVELOPMENT LLC, Wilmington, DE (US)

(72) Inventor: Arockiadoss Thevasahayam, Tamilnadu (IN)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 330 days.

(21) Appl. No.: 14/824,754

(22) Filed: Aug. 12, 2015

(65) Prior Publication Data

US 2016/0045887 A1   Feb. 18, 2016

(30) Foreign Application Priority Data

Aug. 12, 2014 (IN) .......................... 3959/CHE/2014

(51) Int. Cl.
*B01J 19/08* (2006.01)
*C07C 29/34* (2006.01)
(Continued)

(52) U.S. Cl.
CPC ............. *B01J 19/087* (2013.01); *B01J 23/80* (2013.01); *B01J 23/8472* (2013.01); *B01J 31/00* (2013.01);
(Continued)

(58) Field of Classification Search
CPC ........ B01J 19/087; B01J 35/002; B01J 23/80; B01J 23/8472; B01J 37/16; B01J 37/031;
(Continued)

(56) References Cited

U.S. PATENT DOCUMENTS 2,352,791 A   7/1944   Krumboltz et al.
2,607,807 A   8/1952   Ford et al.
(Continued)

FOREIGN PATENT DOCUMENTS

JP   2001046874 A   2/2001

OTHER PUBLICATIONS

Dejardin et al, "Effect of a dc bias field on the dynamic hysteresis of single-domain ferromagnetic particles," J. Appl. Phys. 107, 073914 (2010).*

(Continued)

*Primary Examiner* — Ibrahime A Abraham
*Assistant Examiner* — Colleen M Raphael

(57) ABSTRACT

Described herein is a method of converting a first alcohol to a second alcohol that includes forming a mixture including a superparamagnetic catalyst and a feedstock, wherein the feedstock includes the first alcohol, and exposing the mixture to a fluctuating magnetic field to form a product, wherein the product includes a second alcohol having a longer carbon chain length than the first alcohol. A flow-through method is described for converting a first alcohol to a second alcohol, wherein the second alcohol has a longer carbon chain length than the first alcohol. Also described is a method of converting glycerol to butanol that includes forming a mixture including a superparamagnetic catalyst and a feedstock, wherein the feedstock includes glycerol, and exposing the mixture to a fluctuating magnetic field to form a product, wherein the product includes butanol. A flow-through method is described for converting glycerol to butanol.

18 Claims, 4 Drawing Sheets

(51) Int. Cl.
*B01J 31/00* (2006.01)
*B01J 37/16* (2006.01)
*B01J 23/80* (2006.01)
*B01J 35/00* (2006.01)
*B01J 37/03* (2006.01)
*B01J 23/847* (2006.01)

(52) U.S. Cl.
CPC ......... *B01J 35/002* (2013.01); *B01J 35/0013* (2013.01); *B01J 37/031* (2013.01); *B01J 37/16* (2013.01); *C07C 29/34* (2013.01); *B01J 2219/0854* (2013.01); *B01J 2219/0877* (2013.01); *B01J 2219/0892* (2013.01)

(58) Field of Classification Search
CPC .............................. B01J 35/0013; B01J 31/00; B01J 2219/0892; B01J 2219/0854; B01J 2219/0877; C07C 29/34
USPC ................................ 204/157.9, 155
See application file for complete search history.

(56) References Cited

U.S. PATENT DOCUMENTS

| | | | |
|---|---|---|---|
| 4,517,391 A | 5/1985 | Schuster et al. | |
| 4,810,401 A | 3/1989 | Mair et al. | |
| 5,411,730 A | 5/1995 | Kirpotin et al. | |
| 5,763,353 A | 6/1998 | Kadono et al. | |
| 7,863,489 B2 | 1/2011 | Johnston et al. | |
| 8,518,853 B2 | 8/2013 | Kim et al. | |
| 2002/0106314 A1 | 8/2002 | Pelrine et al. | |
| 2003/0050516 A1 | 3/2003 | Fischer et al. | |
| 2004/0026028 A1 | 2/2004 | Kirsten et al. | |
| 2006/0102871 A1 | 5/2006 | Wang et al. | |
| 2007/0142648 A1 | 6/2007 | Urtel et al. | |
| 2009/0054707 A1* | 2/2009 | Kourtakis | C07C 29/34 568/905 |
| 2010/0197485 A1 | 8/2010 | Johnston et al. | |
| 2010/0249404 A1* | 9/2010 | Friese | B01J 8/42 544/106 |
| 2011/0263910 A1 | 10/2011 | Johnston et al. | |
| 2011/0282109 A1 | 11/2011 | Johnston et al. | |
| 2011/0301363 A1* | 12/2011 | Friese | B01J 8/0285 549/290 |
| 2011/0319672 A1* | 12/2011 | Liu | B01J 21/066 568/863 |
| 2012/0030995 A1 | 2/2012 | Johnston et al. | |
| 2012/0203021 A1* | 8/2012 | Friese | C07C 253/30 558/443 |
| 2012/0253085 A1 | 10/2012 | Johnston et al. | |
| 2012/0283449 A1* | 11/2012 | Friese | B01J 8/0496 549/79 |
| 2013/0345478 A1 | 12/2013 | Wollrab et al. | |

OTHER PUBLICATIONS

Celanese patents acetic acid to ethanol conversion process, accessed at http://www.biofuelsdigest.com bdigest/2011/01/10/celanese-patents-acetic-acid-to-ethanol-conversion-process/, posted on Jan. 10, 2011, pp. 1-3.

Cost-saving measure to upgrade ethanol to butanol—a better alternative to gasoline, *American Chemical Society (ACS)* (Apr. 11, 2013), pp. 1-7.

Ethanoic acid, accessed at http://www.rod.beavon.clara.net/aceticac.htm, pp. 1-3, accessed on Jul. 17, 2015.

Kao et al., Enhancing butanol production with Clostridium pasteurianum CH4 using sequential glucoseglycerol addition and simultaneous dualsubstrate cultivation strategies, (Oct. 13, 2012), 135:324-330.

Ramos Sanchez et al., Butanol Production From Glycerol by Clostridium Pasteurianum in Defined Culture Media—A Phenotypic Approach, (2009), pp. 1-100.

Stombaugh et al., Butanol: The New Biofuel, Cooperative Extension Service University of Kentucky College of Agriculture, Issue 3, pp. 1-2 (2012).

Wang et al., Tuning the Reactivity of Oxide Surfaces by Charge-Accepting Adsorbates, (Sep. 24, 2007), 46(38):7315-7318.

"Chemical Information Search," Chemindustry, accessed at http://www.chemindustry.com/chemicals/26481.html, Copyright 1999-2018, pp. 2.

"O2-A2 Oxygen Sensor," Apollo Optronics, accessed at https://apollounion.en.ec21.com/O2_A2_Oxygen_Sensor-5788327_5787965.html, Copyright 1997-2017, pp. 3.

Delmar, "Infrared: Interpretation," ChemWiki, accessed at https://web.archive.org/web/20120425224929/http://chemwiki.ucdavis.edu/Wikitexts/UCD_Chem_205:_Larsen/ChemWiki_Module_Topics/Infrared:_Interpretation, modified on Nov. 26, 2010, pp. 12.

Zhu, Y., and Jones, S.B., "Techno-economic Analysis for the Thermochemical Conversion of Lignocellulosic Biomass to Ethanol via Acetic Acid Synthesis," U.S. Department of Energy, pp. 79 (Apr. 2009).

* cited by examiner

AREA-1ST QUAD : 4251.7 erg/g   AREA-2ND QUAD : 218.38 erg/g   AREA-3RD QUAD : 5212.6 erg/g
AREA-4TH QUAD : 580.49 erg/g   AREA-TOTAL : 10.263E+3 erg/g   COERCIVITY (Hci) : 127.78 G
MAGNETIZATION (Ms) : 21.645 emu/g   MASS : 3.5000E-3 g   RETENTIVITY (Mr) : 3.1843 emu/g

METHODS, MATERIALS, AND SYSTEMS FOR CONVERTING ALCOHOLS

CLAIM OF PRIORITY

This application claims foreign priority under 35 U.S.C. § 119(a) to Indian Patent Application Na 3959/CHE/2014, filed Aug. 12, 2014 and entitled "METHODS, MATERIALS AND SYSTEMS FOR CONVERTING ALCOHOLS" the disclosure of which is incorporated by reference in its entirety and for all purposes.

BACKGROUND

Alcohols are important commodity feedstock for a variety of industrial products. For example, glycerol is a waste by-product from biodiesel processing that can be used as a feedstock for the production of numerous commodity chemicals. Some of the existing methods use microbial processes for converting glycerol feedstock to usable chemicals such as butanol. Such processes result in a very slow conversion with a relatively low yield. Other methods involve catalytic processes which require very high temperatures and pressures. Thus, there is a need for a faster and more economical process to convert alcohols with shorter carbon chain lengths to alcohols with longer carbon chain lengths, for instance, for converting glycerol feedstock to butanol.

SUMMARY

In an embodiment, a method of converting a first alcohol to a second alcohol includes forming a mixture including a superparamagnetic catalyst and a feedstock, wherein the feedstock includes the first alcohol, and exposing the mixture to a fluctuating magnetic field to form a product, wherein the product includes a second alcohol having a longer carbon chain length than the first alcohol.

In an embodiment, a flow-through method of converting a first alcohol to a second alcohol includes passing a feedstock including a first alcohol having a carbon chain of first length through a reaction chamber containing a superparamagnetic catalyst and exposing the feedstock to a fluctuating magnetic field within the reaction chamber to form a product including a second alcohol having a carbon chain of second length, wherein the second length is longer than the first length.

In an embodiment, a method of converting glycerol to butanol includes forming a mixture including a superparamagnetic catalyst and a feedstock, wherein the feedstock includes glycerol, and exposing the mixture to a fluctuating magnetic field to form a product, wherein the product includes butanol.

In an embodiment, a flow-through method of converting glycerol to butanol includes passing a feedstock including glycerol through a reaction chamber containing a superparamagnetic catalyst and exposing the feedstock to a fluctuating magnetic field within the reaction chamber to form a product including butanol.

BRIEF DESCRIPTION OF THE DRAWINGS

The drawings submitted herewith show some embodiments or features of some embodiments encompassed by the disclosure. The drawings are meant to be illustrative and are not intended to be limiting.

DETAILED DESCRIPTION

Because existing processes for synthesizing alcohols, such as preparing butanol from glycerol, often require expensive catalysts and/or long periods of time to complete, a faster and more economical process is desirable.

The technology described herein generally relates to a method of converting a first alcohol to a second alcohol, wherein the second alcohol has a longer carbon chain length than the first alcohol. The methods described herein are based, at least in part, on exposing a mixture including a first alcohol and a superparamagnetic catalyst to a fluctuating magnetic field.

Figure 1:
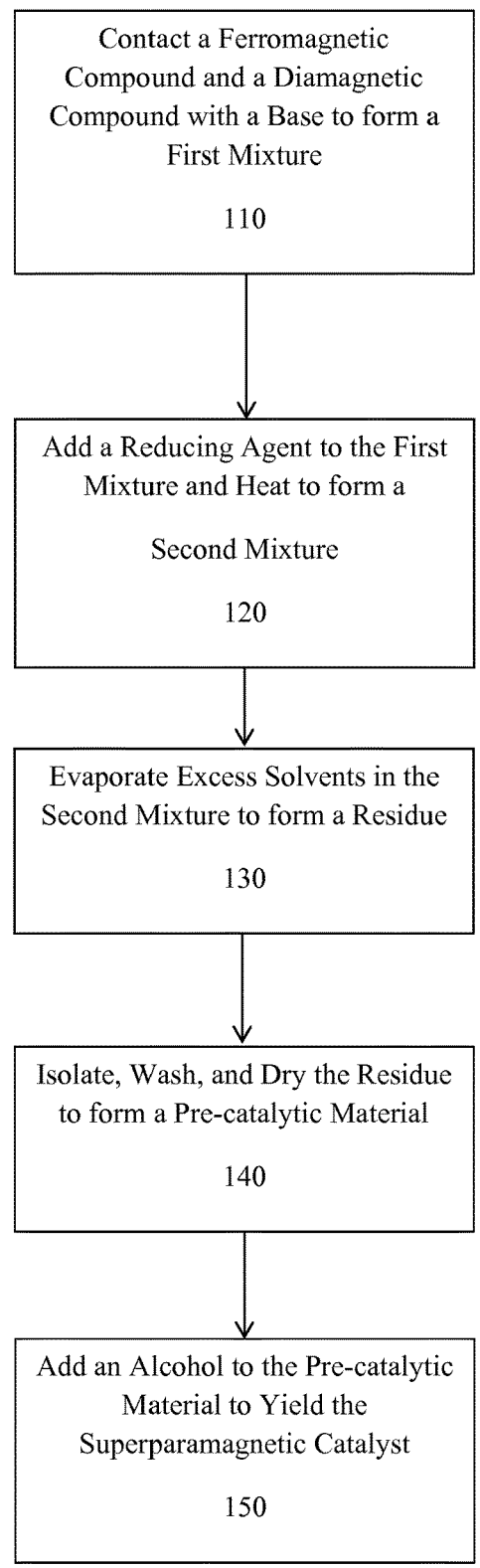
FIG. 1 is a flow diagram of a method of synthesizing a superparamagnetic catalyst in accordance with some embodiments described herein.

As used herein, "superparamagnetic catalyst" refers to one or more particles having a single magnetic domain having two stable and antiparallel magnetic moments, between which the material may transition at temperatures below the Curie temperature of the material. FIG. 1 is a flow diagram of a method of synthesizing a superparamagnetic catalyst in accordance with some embodiments described herein. Generally, some methods of synthesizing a superparamagnetic catalyst may include contacting a ferromagnetic compound and a diamagnetic compound with a base to form a first mixture 110, adding a reducing agent to the first mixture 110 and heating to form a second mixture 120, evaporating the excess solvents in the second mixture 120 to form a residue 130, isolating, washing, and drying the residue 130 to form a pre-catalytic material 140, and adding an alcohol to the pre-catalytic material 140 to yield the superparamagnetic catalyst 150. Each of these steps is discussed in detail below.

In some embodiments, a ferromagnetic compound and a diamagnetic compound are contacted with a base to form a first mixture 110. In some embodiments, the ferromagnetic compound includes an oxide. In some embodiments, the ferromagnetic compound includes $Fe_2O_3$, $MN_2O_3$, $NI_2O_3$, or combinations thereof. In some embodiments, the ferromagnetic compound includes $Fe_2O_3$. In some embodiments, the diamagnetic compound includes a chloride salt. In some embodiments, the diamagnetic compound includes $ZnCl_2$, cadmium chloride, nickel chloride, copper chloride, or combinations thereof. In some embodiments, the diamagnetic compound includes $ZnCl_2$. In some embodiments, the weight to weight ratio of the ferromagnetic compound to the diamagnetic compound is about 2:1. In some embodiments, the weight to weight ratio of the ferromagnetic compound to the diamagnetic compound is about 1:1. In some embodiments, the base comprises NaOH, LiOH, KOH, RbOH, CsOH, CaOH, or combinations thereof. In some embodiments, the base comprises NaOH. The base may generally have any concentration. In some embodiments, the base has a concentration of about 5.5 N to about 6.5 N, or any concentration or range of concentrations between about 5.5 N and about 6.5 N, inclusive. In some embodiments, the base has a concentration of about 6 N. In some embodiments, the base is NaOH and has a concentration of about 6 N. In some embodiments, the ferromagnetic compound and the diamagnetic compound are dissolved in the base with stirring. In some embodiments, the ferromagnetic compound and the diamagnetic compound are dissolved in the base and stirred for about 5 minutes to about 10 minutes, or any time or range of times between about 5 minutes and about 10 minutes, inclusive.

In some embodiments, a reducing agent is added to the first mixture 110 and heated to form a second mixture 120. In some embodiments, the reducing agent includes $NaBH_4$, hydrazine hydroxide, or combinations thereof. In some embodiments, the reducing agent includes $NaBH_4$. In some embodiments, the reducing agent has a concentration of about 0.05 N to about 1 N. In some embodiments, the reducing agent has a concentration of about 0.5 N. In some embodiments, the reducing agent has a concentration of about 0.06 N. In some embodiments, the reducing agent has a concentration of about 0.05 N, about 0.06 N, about 0.5 N, about 1 N, or any concentration or range of concentrations between about 0.05 N and about 1 N, inclusive of endpoints. In some embodiments, the reducing agent is $NaBH_4$ and has a concentration of about 0.06 N. In some embodiments, the reducing agent is added in a drop-wise fashion. In some embodiments, the reducing agent is added in a continuous fashion. In some embodiments, the heating is at a temperature of about 95° C. to about 105° C. In some embodiments, the heating is at a temperature of about 100° C. In some embodiments, the heating is at a temperature of about 95° C., about 100° C., about 105° C., or any temperature or range of temperatures between about 95° C. and 105° C., inclusive of endpoints. In some embodiments, the heating occurs for about 45 minutes to about 75 minutes. In some embodiments, the heating occurs for about 60 minutes. In some embodiments, the heating occurs for about 45 minutes, about 60 minutes, about 75 minutes, or any number of minutes or range of minutes between about 45 minutes and about 75 minutes, inclusive of endpoints.

In some embodiments, any excess solvents in the second mixture 120 are evaporated to form a residue 130. In some embodiments, the evaporating occurs at a temperature of about 105° C. to about 115° C. In some embodiments, the evaporating occurs at a temperature of about 110° C. In some embodiments, the evaporating occurs at a temperature of about 105° C., about 110° C., about 115° C., or any temperature or range of temperatures between about 105° C. and 115° C., inclusive of endpoints. In some embodiments, a Soxhlet setup is used to evaporate the excess solvents.

In some embodiments, the residue 130 is isolated, washed, and dried to form a pre-catalytic material 140. In some embodiments, the residue is washed with distilled water. In some embodiments, the residue is washed until a pH of about 7 is reached. In some embodiments, the residue is dried by placing in a furnace. In some embodiments, the residue is dried at a temperature of about 500° C. to about 550° C. In some embodiments, the residue is dried at a temperature of about 500° C. In some embodiments, the residue is dried at a temperature of about 500° C., about 550° C., or any temperature or range of temperatures between about 500° C. to about 550° C., inclusive of endpoints. In some embodiments, the residue is dried for about 3 minutes to about 5 minutes. In some embodiments, the residue is dried for about 3 minutes, about 5 minutes, or any time or range of times between about 3 minutes and about 5 minutes, inclusive of endpoints. In some embodiments, the residue is dried for about 1 hour.

In some embodiments, an alcohol is added to the pre-catalytic material 140 to yield the superparamagnetic catalyst 150. In some embodiments, the alcohol is ethanol, methanol, propanol, butanol, or combinations thereof. In some embodiments, the alcohol is ethanol. In some embodiments, the superparamagnetic catalyst is $Fe_2ZnO_4$.

In some embodiments, the superparamagnetic catalyst comprises $Fe_2ZnO_4$, produced by the method described in FIG. 1, in which the ferromagnetic compound is $Fe_2O_3$, the diamagnetic compound is $ZnCl_2$, the base is NaOH, the reducing agent is $NaBH_4$, and the alcohol is ethanol. In some embodiments, the superparamagnetic catalyst $Fe_2ZnO_4$ comprises particles with an average particle diameter of about 50 nm to about 100 nm, or any average particle diameter or range of average particle diameters between about 50 nm and about 100 nm, inclusive. In some embodiments, the superparamagnetic catalyst further comprises at least one of CO, Ni, and V.

Figure 2:
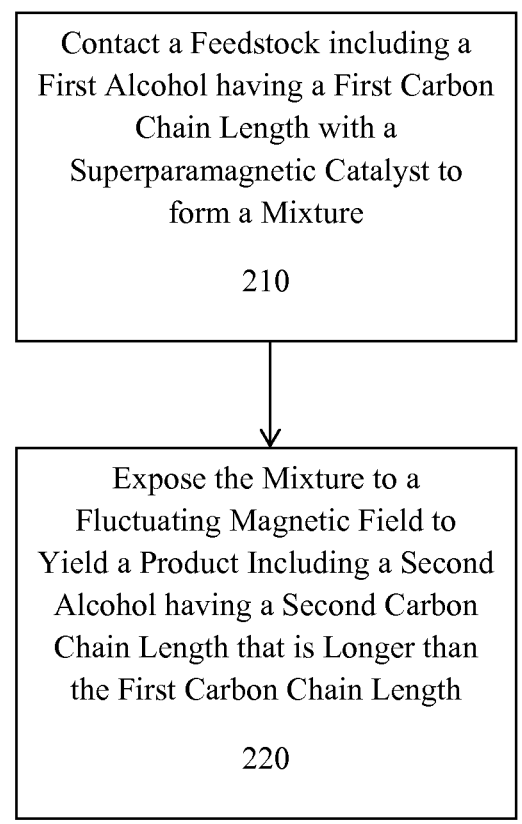
FIG. 2 is a flow diagram of a method of converting a first alcohol to a second alcohol in accordance with some embodiments described herein.

The superparamagnetic catalyst produced according to the method described herein may be used in any embodiments describing methods for converting a first alcohol to a second alcohol described herein. FIG. 2 is a flow diagram of a method of converting a first alcohol to a second alcohol in accordance with some embodiments described herein.

In some embodiments, a feedstock including a first alcohol having a carbon chain of first length is contacted 210 with a superparamagnetic catalyst to form a mixture, and the mixture is exposed 220 to a fluctuating magnetic field to yield a product including a second alcohol having a carbon chain of second length, wherein the second length is longer than the first length. As used herein, the phrase "carbon chain of first length" means the total number of carbon atoms in the first alcohol. As used herein, the phrase "carbon chain of second length" means the total number of carbon atoms in the second alcohol.

The conversion of a first alcohol to a second alcohol having a longer carbon chain length than the first alcohol (meaning the total amount of carbon atoms in the second alcohol is greater than the total number of carbon atoms in the first alcohol) can be performed using a batch process, a continuous flow-through method, or a non-continuous flow-through method, and some embodiments utilize a flow-through system. In some embodiments, the method of converting a first alcohol to a second alcohol is performed at ambient conditions, in some instances at a pressure of about 100 kPa, and/or in some instances at a temperature of about 25° C. to about 35° C.

This disclosure is not limited to the particular systems, devices, and methods described, as these may vary. The terminology used in the description is for the purpose of describing the particular versions or embodiments only, and is not intended to limit the scope.

Some embodiments include converting a first alcohol having a carbon chain of first length to a second alcohol having a carbon chain of second length, wherein the second length is greater than the first length. The first alcohol can include one or more of any alcohol(s). In some embodiments, the first alcohol contains about 1 to about 8 carbon atoms and at least one hydroxyl group. In some embodiments, the first alcohol contains about 1 to about 8 carbon atoms arranged in a straight chain or branched chain, either of which is saturated, unsaturated, or partially unsaturated. In some embodiments, the first alcohol comprises glycerol, ethanol, butanol, propanol, methanol, or combinations thereof. In some embodiments, the first alcohol is glycerol. In some embodiments, the first alcohol includes glycerol. In some embodiments, the first alcohol has a carbon chain length of about 1 to about 8 carbons. The second alcohol can include one or more of any alcohol(s). In some embodiments, the second alcohol contains about 2 to about 16 carbon atoms and at least one hydroxyl group. In some embodiments, the second alcohol contains about 2 to about 16 carbon atoms arranged in a straight chain or a branched chain, either of which is saturated, unsaturated, or partially unsaturated. In some embodiments, the second alcohol comprises butanol, octanol, propanol, ethanol, Bio-oil, Soi-oil, or combinations thereof. In some embodiments, the second alcohol is butanol. In some embodiments, the second alcohol includes butanol. In some embodiments, the second alcohol has a carbon chain length of about 2 to about 16 carbons. In some embodiments, the first alcohol is glycerol and the second alcohol is butanol. In some embodiments, the first alcohol includes glycerol and the second alcohol includes butanol. In any of the embodiments described herein, the butanol may be 1-butanol, 2-butanol, 2-methyl-1-propanol, 2-methyl-2-propanol, or combinations thereof. In some embodiments, the butanol is substantially 2-methyl-2-propanol. In some embodiments, the butanol is 2-methyl-2-propanol.

In some embodiments, a method for converting a first alcohol to a second alcohol includes contacting a superparamagnetic catalyst and a feedstock to form a mixture. Contacting may be accomplished by any suitable means, including mixing, stirring, combining, shaking, agitation, and the like.

In some embodiments, the superparamagnetic catalyst is made using the methods described herein. In some embodiments, the superparamagnetic catalyst is in particle form, and the particles have an average diameter of about 50 nm to about 100 nm. In some embodiments, the superparamagnetic catalyst is $Fe_2ZnO_4$. In some embodiments, the superparamagnetic catalyst is $Fe_2ZnO_4$, and it is in a particle form. In some embodiments, the particles have an average diameter of about 50 nm to about 100 nm. In some embodiments, the superparamagnetic catalyst includes $Fe_2ZnO_4$, and further includes at least one of Co, Ni, V, or combinations thereof.

In some embodiments, the feedstock includes the first alcohol. In some embodiments, the feedstock includes about 1 v/v % to about 100 v/v % of the first alcohol, or any v/v % or range of v/v % between about 1 v/v % and about 100 v/v %, inclusive of endpoints. In some embodiments, the feedstock includes about 75 v/v % of the first alcohol. In some embodiments, the feedstock includes about 1 v/v % to about 100 v/v % of glycerol, or any v/v % or range of v/v % between about 1 v/v % and about 100 v/v %, inclusive of endpoints. In some embodiments, the feedstock includes about 75 v/v % of glycerol. In some embodiments, the feedstock further includes water. In some embodiments the feedstock includes about 1 v/v % to about 99 v/v % water, or any v/v % or range of v/v % between about 1 v/v % and about 99 v/v %, inclusive of endpoints. In some embodiments, the feedstock includes about 25 v/v % water.

In some embodiments, filtration is used to remove any contaminant or contaminants from the feedstock before contacting with the superparamagnetic catalyst. In some embodiments, the feedstock, including at least one contaminant, contacts the superparamagnetic catalyst.

In some embodiments, the feedstock includes the first alcohol, and water is added to the feedstock prior to contacting the feedstock and the superparamagnetic catalyst. In some embodiments, the feedstock includes about 1 v/v % to about 99 v/v % water after adding water to the feedstock, or any v/v % or range of v/v % between about 1 v/v % and about 99 v/v %, inclusive of endpoints. In some embodiments, the feedstock includes about 25 v/v % water after adding water to the feedstock.

In some embodiments, the feedstock includes glycerol, and water is added to the feedstock prior to contacting the feedstock and the superparamagnetic catalyst. In some embodiments, the feedstock includes about 1 v/v % to about 99 v/v % water after adding water to the feedstock, or any v/v % or range of v/v % between about 1 v/v % and about 99 v/v %, inclusive of endpoints. In some embodiments, the feedstock includes about 25 v/v % water after adding water to the feedstock.

In some embodiments, the superparamagnetic catalyst is added to the feedstock to form a mixture. In some embodiments, the feedstock is added to the superparamagnetic catalyst to form a mixture. In some embodiments, the mixture contains about 100 mg to about 500 mg of the superparamagnetic catalyst to every about 2 ml to about 20 ml of first alcohol, or any number or range of numbers between about 100 mg and about 500 mg and about 2 ml to about 20 ml, inclusive of endpoints. In some embodiments, the mixture contains about 400 mg of the superparamagnetic catalyst to every about 15 ml of first alcohol.

In some embodiments, the mixture includes the superparamagnetic catalyst and the feedstock. In some embodiments, the mixture includes the superparamagnetic catalyst and the first alcohol. In some embodiments, the mixture includes the superparamagnetic catalyst, the first alcohol, and water. In some embodiments, the mixture includes the superparamagnetic catalyst, the first alcohol, and at least one contaminant. In some embodiments, the mixture includes the superparamagnetic catalyst, the first alcohol, water, and at least one contaminant. In some embodiments, at least one contaminant is removed from the mixture before exposing the mixture to a fluctuating magnetic field. In some embodiments, filtration is used to remove at least one contaminant from the mixture before exposing the mixture to a fluctuating magnetic field.

In some embodiments, the mixture is exposed to a fluctuating magnetic field to form a product. The fluctuating magnetic field may be created by any suitable means. In some embodiments, the fluctuating magnetic field is supplied by an alternating current electromagnet. In some embodiments, the fluctuating magnetic field is supplied by a solenoid magnet. In some embodiments, the fluctuating magnetic field has a field strength of at least about 300 milliTesla. In some embodiments, the fluctuating magnetic field has a field strength of about 300 milliTesla to about 600 milliTesla, or any field strength or range of field strengths between about 300 milliTesla and 600 milliTesla, inclusive. In some embodiments, the fluctuating magnetic field has a field strength of about 300 milliTesla. In some embodiments, the fluctuating magnetic field has a fluctuation frequency of about 48 Hz to about 52 Hz, or any fluctuation frequency or range of fluctuation frequencies between about 48 Hz and about 52 Hz, inclusive. In some embodiments, the fluctuating magnetic field has a fluctuation frequency of about 50 Hz. In some embodiments, the fluctuating magnetic field has a fluctuation frequency of about 48 Hz, about 50 Hz, about 52 Hz, or any frequency or range of frequencies between about 48 Hz and about 52 Hz, inclusive of endpoints. In some embodiments, the mixture is exposed to the fluctuating magnetic field for about 1 minute to about 60 minutes. In some embodiments, the mixture is exposed to the fluctuating magnetic field for about 10 minutes to about 30 minutes. In some embodiments, the mixture is exposed to the fluctuating magnetic field for about 10 minutes to about 15 minutes. In some embodiments, the mixture is exposed to the fluctuating magnetic field for about 1 minute, about 10 minutes, about 15 minutes, about 30 minutes, about 60 minutes, or any time or range of times between 1 minute and 60 minutes, inclusive of endpoints.

In some embodiments, the mixture is heated to a temperature of about 30° C. to about 45° C., or any temperature or range of temperatures between about 30° C. and about 45° C., inclusive of endpoints.

In some embodiments, the product includes the second alcohol having a carbon chain of second length. In some embodiments, the product includes the second alcohol and the superparamagnetic catalyst. In some embodiments, the product includes the second alcohol and water. In some embodiments, the product includes the second alcohol, the superparamagnetic catalyst, and water. In some embodiments, the product includes the second alcohol and at least one contaminant. In some embodiments, the product includes the second alcohol, the superparamagnetic catalyst, and at least one contaminant. In some embodiments, the product includes the second alcohol, water, and at least one contaminant. In some embodiments, the product includes the second alcohol, the superparamagnetic catalyst, water, and at least one contaminant. In some embodiments, water is removed from the product. In some embodiments, water is removed from the product by distillation. In some embodiments, at least one contaminant is removed from the product. In some embodiments, filtration is used to remove at least one contaminant from the product. In some embodiments, water and at least one contaminant is removed from the product.

In some embodiments, the superparamagnetic catalyst is recovered from the product. In some embodiments, the superparamagnetic catalyst is recovered from the product by filtration. In some embodiments, the superparamagnetic catalyst is recovered from the product by magnetic separation. In some embodiments, the magnetic separation includes using simple magnets.

In some embodiments, water is removed from the product after the superparamagnetic catalyst is recovered from the product. In some embodiments, water is removed from the product by distillation. In some embodiments, at least one contaminant is removed from the product after the superparamagnetic catalyst is recovered from the product. In some embodiments, at least one contaminant is removed from the product by filtration. In some embodiments, water and at least one contaminant are removed from the product after the superparamagnetic catalyst is recovered.

In some embodiments, the percent yield of the second alcohol from the first alcohol is about 1% to about 100%. In some embodiments, the percent yield of the second alcohol from the first alcohol is about 15% to about 78%. In some embodiments, the percent yield of the second alcohol from the first alcohol is about 50%. In some embodiments, the percent yield of the second alcohol from the first alcohol is about 1%, about 15%, about 50%, about 78%, about 100%, or any percent or range of percents between about 1% and about 100%, inclusive of endpoints. In some embodiments, the first alcohol includes glycerol and the second alcohol includes butanol, and the percent yield of butanol from glycerol is about 1% to about 100%. In some embodiments, the first alcohol includes glycerol and the second alcohol includes butanol, and the percent yield of butanol from glycerol is about 15% to about 78%. In some embodiments, the first alcohol includes glycerol and the second alcohol includes butanol, and the percent yield of butanol from glycerol is about 50%. In some embodiments, the first alcohol includes glycerol and the second alcohol includes butanol, and the percent yield of butanol from glycerol is about 1%, about 15%, about 50%, about 78%, about 100%, or any percent or range of percents between about 1% and about 100%, inclusive of endpoints.

Any of the embodiments may be performed at ambient conditions, in some instances at a pressure of about 100 kPa, and/or in some instances at a temperature of about 25° C. to about 35° C.

In some embodiments, a flow-through method for converting a first alcohol to a second alcohol includes providing a feedstock including a first alcohol having a carbon chain of a first length, passing the feedstock through a reaction chamber containing a superparamagnetic catalyst, exposing the feedstock to a fluctuating magnetic field within the reaction chamber to form a product including the second alcohol having a carbon chain of second length, wherein the second length is longer than the first length. In some embodiments, the feedstock is continuously passed through the reaction chamber. In some embodiments, the first alcohol includes glycerol and the second alcohol includes butanol.

EXAMPLES

Example 1: Preparation of Superparamagnetic $Fe_2ZnO_4$ Nanoparticle Catalyst Materials Ferric Oxide ($Fe_2O_3$), Nice Chemicals (P) Ltd., India, Code No: F11729, Cas Code: 1309-37-1; Zinc Chloride ($ZnCl_2$), Rankem, India, Cas No: 7646-85-7, Prod. No: Z0020; Sodium Borohydride ($NaBH_4$), Molychem, India, Cas No: 16940-66-2, Prod. No: 18180; Sodium Hydroxide (NaOH), Rankem, India, Cas No: 1310-73-2, Prod. No: 50290.

Process

A Soxhlet apparatus was used in the preparation of the superparamagnetic $Fe_2ZnO_4$ nanoparticle catalyst. First, 2 g of $Fe_2O_3$ and 2 g of $ZnCl_2$ were dissolved in 6N NaOH solution by continuously stirring for 5-10 minutes. 50 ml of water was added to the mixture. To this solution, 0.06 N $NaBH_4$ was added drop by drop and placed in a magnetic stirrer for 1 hour at 100° C. This solution was then transferred to the Soxhlet setup and maintained at 110° C. until all of the excess solvents were evaporated. The remaining residue was washed with distilled water until a pH of about 7 was reached. After filtering the solution, the residue was dried in a furnace for 1 hour at 500° C. and then it was removed. 10 ml of ethanol was immediately added, and the resulting product was a superparamagnetic $Fe_2ZnO_4$ nanoparticle catalyst.

Figure 3A:
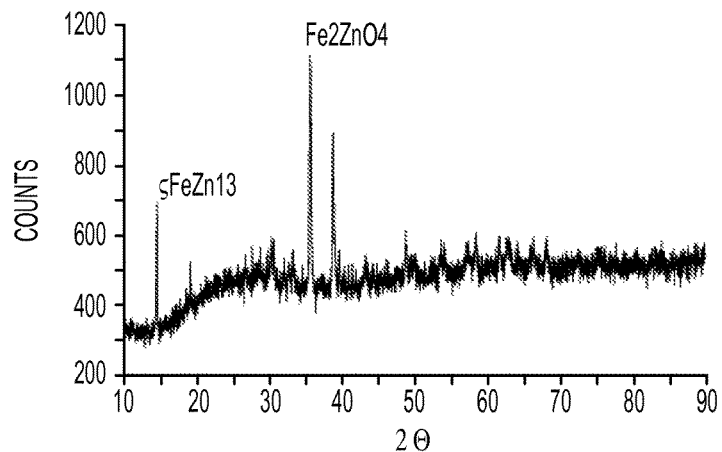
FIG. 3A is an XRD (Pan analytic Xperts) characterization of a paramagnetic $Fe_2ZnO_4$ nanoparticle catalyst in accordance with some embodiments. The x-axis is 2 θ, and the y-axis is counts.
Figure 3B:
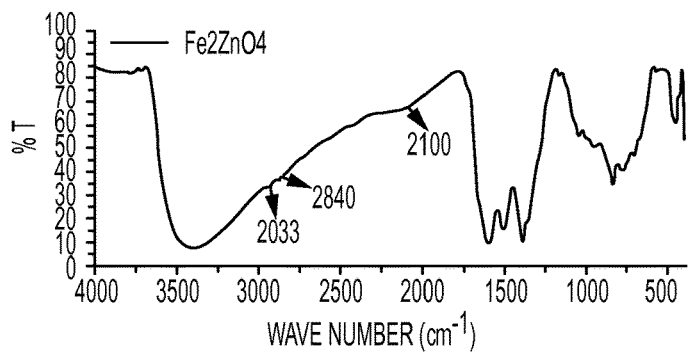
FIG. 3B is an FTIR spectrum (FTIR spectrum-Bruker V500) characterization of a paramagnetic $Fe_2ZnO_4$ nanoparticle catalyst in accordance with some embodiments. The x-axis is wave number in $cm^{-1}$, and the y-axis is percent transmission.
Figure 3C:
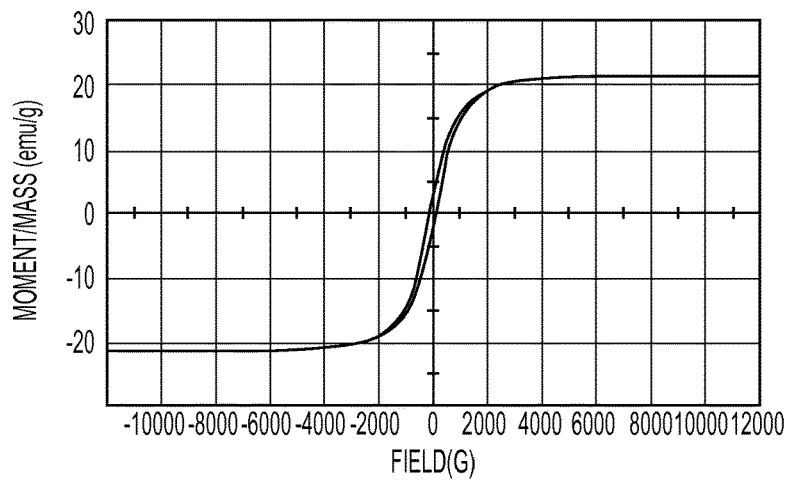
FIG. 3C is a VSM spectrum (VSM-Bruker) characterization of a paramagnetic $Fe_2ZnO_4$ nanoparticle catalyst in accordance with some embodiments.

Example 2: Characterization of the Superparamagnetic $Fe_2ZnO_4$ Nanoparticle Catalyst The superparamagnetic $Fe_2ZnO_4$ nanoparticle catalyst was characterized by XRD-Pan analytic Xperts, FTIR spectrum-Bruker V500, and VSM-Bruker, and the results are shown in FIG. 3. FIG. 3A shows that an XRD of $Fe_2ZnO_4$ indicated that it was a polycrystalline material acquired on an Xperts Pananalytical X-Ray diffractometer using Ni-filtered CuKα radiation (λ=0.15418 nm) with scanning range (2θ) of 10 to 90. The peak 2θ at 14.58 corresponds to Iron zinc (ξFeZnl3) of pcpdf file—65-4676 and Millar indices (h k l) value (1 1 0) and 35.56 at 2θ peak corresponding to Iron zinc oxide ($Fe_2ZnO_4$) of pcpdf file 74-1510 and Millar indices (h k l) value (0 0 1). A FTIR spectrum as shown in FIG. 3B confirms the metal oxide peaks at 2900 and 2100 $cm^{-1}$. FIG. 3C shows that a VSM indicated that the material had a coercivity of 5212 G, and has superparamagnetic behavior.

Example 3: Use of Superparamagnetic $Fe_2ZnO_4$ Nanoparticle Catalyst

First, 20 ml of glycerol was mixed with 5 ml of water and stirred well for 3-4 minutes. The water was added to inhibit undesirable reactions. Next, 5 mg of the catalyst $Fe_2ZnO_4$ nanoparticles was dispersed/mixed in the glycerol and water solution in a vessel. The vessel containing the mixture of glycerol, water, and $Fe_2ZnO_4$ catalyst was subjected to electromagnetic induction heating, at a power level of 250 V 30 MHz for 10-15 minutes. The gases that were evolved were collected and subsequently analyzed. The resulting mixture contained butanol. Finally, the $Fe_2ZnO_4$ catalyst was recovered using simple 0.03 T magnets.

All of the reactions were carried out at standard temperature and pressure.

Example 4: Confirmatory Test of the Products

A test was used to determine the presence of butanol. Five samples were obtained: (1) butanol obtained from the process according to Example 3 ("sample test" butanol); (2) commercially available butanol; (3) commercially available propanol; (4) commercially available ethanol; and (5) commercially available methanol.

10 drops each of methanol, ethanol, propanol, commercially available butanol, and the "sample test" butanol were added to different test tubes. 25 drops of iodine solution and 10 drops of sodium hydroxide solution were added to each test tube. The test tubes were each gently swirled a few times. After a few minutes, the commercially available butanol and the "sample test" butanol were observed to change to a greenish-yellow color. The other alcohols remained clear.

Additionally, while distilling the product obtained from the process according to Example 3, one of the products was recovered at about 81-83° C., while the water was recovered at approximately 97-99° C. This indicates that the product obtained from the process according to Example 3 was ter-butanol, because ter-butanol has a boiling point of about 82° C., while 1-butanol has a boiling point of about 115° C.

Figure 4A:
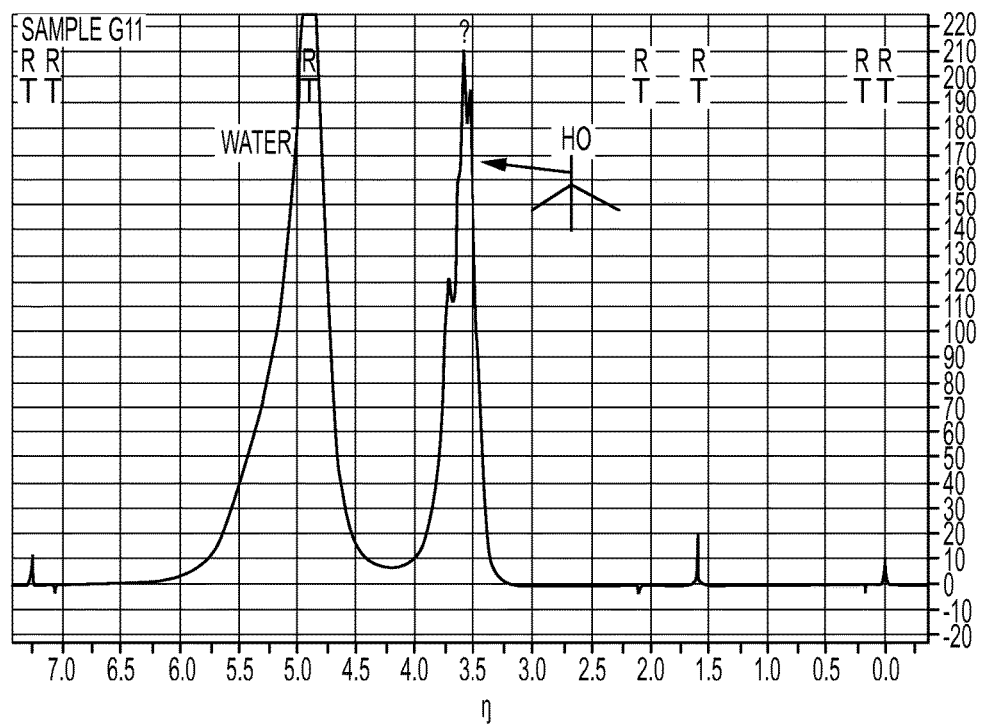
FIG. 4A and FIG. 4B shows $^1H$ and $^{13}C$ NMR spectrum of ter-butanol produced in accordance with some embodiments. The x-axis is ppm, and the y-axis is intensity.
Figure 4B:
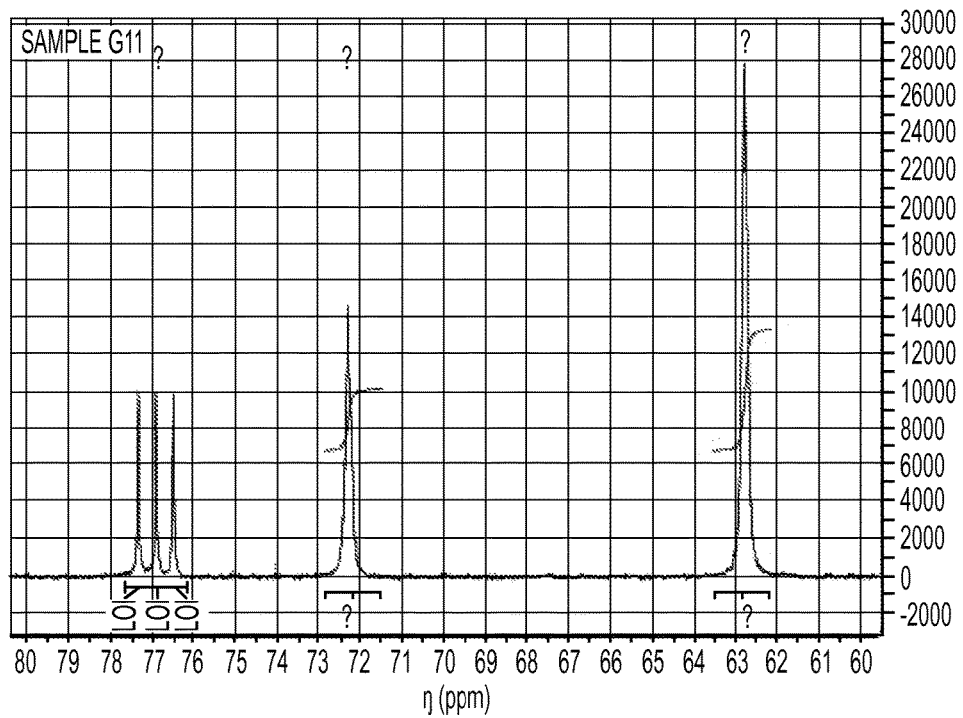

FIG. 4 shows (a) 1H and (b) 13C NMR spectrum of ter-butanol, determined by $CDCl_3$, the hydroxylic proton exchange coupling by singlet at δ 4.9 and tetra at δ 3.71, δ 3.59, δ 3.55, δ 3.53, and δ 1.59. The 13C NMR spectrum of ter-butanol is determined by $CDCl_3$. The C13 NMR observed corroborated with publicly available C13NMR. Thus, ter-butanol is formed when a mixture of glycerol and water is subjected to a hyperthermia process in the presence of $Fe_2ZnO_4$ catalyst.

Example 5: Yield Analysis

Various experiments were carried out to find out the optimum process parameters for obtaining a high yield of butanol from a mixture of glycerol and water using the process according to some embodiments. The initial volume of the sample (glycerol+water) was 20 ml in all cases.

An experiment was carried out to determine the effects of catalyst loading on percent yield of butanol. Five samples of 75% glycerol/25% water were exposed to electromagnetic induction for 30 minutes, each with a different amount of catalyst to determine the effects of catalyst loading on the percent yield of butanol. Catalyst amounts for samples 1, 2, 3, 4, and 5 were 100 mg, 200 mg, 300 mg, 400 mg, and 500 mg, respectively. The percent yield of butanol for samples 1, 2, 3, 4, and 5 was 16.3%, 31.3%, 45.85%, 62.9% and 71.5%, respectively. Table 1 shows the yield analysis for the different catalyst loadings. The data indicates that a higher catalyst loading has a higher butanol yield when percent glycerol, percent water, and time of exposure to electromagnetic induction remain the same.

TABLE 1

| Sample No. | Time of Exposure (in min) | Catalyst weight (in mg) | Volume of the sample (20 ml) Gly in % | After reaction volume of the sample; initial vol = 20 ml | Butanol after distillation (in ml) | Water: Glycerol (ml:ml) remaining after process | Butanol Yield % |
|---|---|---|---|---|---|---|---|
| 1 | 30 | 100 | 75% | 19.0 | 3.1 ± 0.2 | 3:12.9 | 16.3 |
| 2 | 30 | 200 | 75% | 16.9 | 5.3 ± 0.2 | 3:8.6 | 31.3 |
| 3 | 30 | 300 | 75% | 15.7 | 7.2 ± 0.2 | 2:6.1 | 45.85 |
| 4 | 30 | 400 | 75% | 13.5 | 8.5 ± 0.2 | 1.8:3.2 | 62.9 |
| 5 | 30 | 500 | 75% | 12.3 | 8.8 ± 0.2 | 1.5:3.2 | 71.5 |

An experiment was carried out to determine the effects of the glycerol to water ratio on the percent yield of butanol. Five samples having various glycerol to water ratios were exposed to electromagnetic induction for 30 minutes with a catalyst load of 400 mg to determine the effects of the glycerol to water ratio on the percent yield of butanol. Percent glycerol for samples 1, 2, 3, 4, and 5 was 100%, 75%, 50%, 25%, and 10%, respectively. The percent yield of butanol for samples 1, 2, 3, 4, and 5 was 15.8%, 29.4%, 57.4%, 62.9%, and 70.7%, respectively. Table 2 shows the yield analysis for the different ratios of glycerol to water. The data indicates that the more water mixed with glycerol, the higher the butanol yield when time of exposure to electromagnetic induction and catalyst loading remain the same.

TABLE 2

| Sample No. | Time of Exposure (in min) | Catalyst weight (in mg) | Volume of the sample (20 ml) Gly in % | After reaction volume of the sample; initial vol = 20 ml | Butanol after distillation (in ml) | Water: Glycerol (ml:ml) remaining after process | Butanol Yield % |
|---|---|---|---|---|---|---|---|
| 1 | 30 | 400 | 100% | 19.5 | 3.1 ± 0.1 | 3.1:16.4 | 15.8 |
| 2 | 30 | 400 | 75% | 18.0 | 5.3 ± 0.2 | 2.6:10.1 | 29.4 |
| 3 | 30 | 400 | 50% | 16.7 | 9.6 ± 0.2 | 2.5:4.1 | 57.4 |
| 4 | 30 | 400 | 25% | 13.5 | 8.5 ± 0.2 | 2.0:3.0 | 62.9 |
| 5 | 30 | 400 | 10% | 14.0 | 9.9 ± 0.1 | 2.0:2.1 | 70.7 |

An experiment was carried out to determine the effects of the length of exposure to electromagnetic induction on the percent yield of butanol. Five samples of 80% glycerol/20% water were exposed to electromagnetic induction for different lengths of time, each sample having a catalyst load of 400 mg, to determine the effects of the length of exposure to electromagnetic induction on the percent yield of butanol. The time of exposure for samples 1, 2, 3, 4, and 5 was 15 minutes, 30 minutes, 45 minutes, 60 minutes, and 75 minutes, respectively. The percent yield of butanol for samples 1, 2, 3, 4, and 5 was 32.4%, 66.6%, 73.0%, 77.1%, and 78.4%, respectively. Table 3 shows the yield analysis for different lengths of exposure to electromagnetic induction. The data indicates that the longer the exposure to electromagnetic induction, the higher the butanol yield when percent glycerol, percent water, and catalyst loading remained the same.

TABLE 3

| Sample No. | Time of Exposure (in min) Time | Catalyst weight (in mg) | Volume of the sample (20 ml) Gly in % | After reaction volume of the sample; initial vol = 20 ml | Butanol after distillation (in ml) | Water: Glycerol (ml:ml) remaining after process | Butanol Yield % |
|---|---|---|---|---|---|---|---|
| 1 | 15 | 400 | 80% | 18.5 | 6 ± 0.2 | 4.5:8.0 | 32.4 |
| 2 | 30 | 400 | 80% | 18 | 12 ± 0.2 | 3.0:3.0 | 66.6 |
| 3 | 45 | 400 | 80% | 17.8 | 13 ± 0.2 | 2.5:2.3 | 73.0 |
| 4 | 60 | 400 | 80% | 17.5 | 13.5 ± 0.2 | 2.3:1.7 | 77.1 |
| 5 | 75 | 400 | 80% | 17.2 | 13.5 ± 0.2 | 2.5:1.2 | 78.4 |

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera As a non-limiting example, each range discussed herein can be readily broken down into a lower third, middle third and upper third, et cetera As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method for converting a first alcohol to a second alcohol, the method comprising:
    contacting a superparamagnetic catalyst and a feedstock to form a mixture, wherein the superparamagnetic catalyst comprises $Fe_2ZnO_4$ and, wherein the feedstock comprises the first alcohol having a carbon chain of a first length; and
    exposing the mixture to a fluctuating magnetic field to form a product, wherein the product comprises the second alcohol having a carbon chain of a second length, wherein the second length is longer than the first length.

2. The method of claim 1, wherein the first alcohol comprises glycerol, ethanol, butanol, propanol, methanol, or combinations thereof.

3. The method of claim 1, wherein the first alcohol comprises glycerol.

4. The method of claim 1, wherein the second alcohol comprises butanol, octanol, propanol, ethanol, or combinations thereof.

5. The method of claim 1, wherein the second alcohol comprises butanol.

6. The method of claim 1, wherein the first alcohol comprises glycerol and the second alcohol comprises butanol.

7. The method of claim 1, wherein the superparamagnetic catalyst comprises particles having an average diameter of about 50 nm to about 100 nm.

8. The method of claim 1, wherein the superparamagnetic catalyst further comprises at least one of Co, Ni, and V.

9. The method of claim 1, wherein the mixture comprises about 100 mg to about 500 mg of superparamagnetic catalyst to every about 2 ml to 20 ml of first alcohol.

10. The method of claim 1, wherein the mixture comprises about 400 mg of superparamagnetic catalyst to every about 15 ml of first alcohol.

11. The method of claim 1, wherein the fluctuating magnetic field has a field strength of at least about 300 milliTesla.

12. The method of claim 1, wherein the fluctuating magnetic field has a field strength of about 300 milliTesla to about 600 milliTesla.

13. The method of claim 1, wherein the fluctuating magnetic field has a fluctuation frequency of about 48 Hz to about 52 Hz.

14. The method of claim 1, wherein the fluctuating magnetic field is supplied by an alternating current electromagnet.

15. The method of claim 1, wherein the mixture is heated to a temperature of about 30° C. to about 45° C.

16. The method of claim 1, wherein the mixture is exposed to the fluctuating magnetic field for about 1 minute to about 60 minutes.

17. The method of claim 1, further comprising recovering the superparamagnetic catalyst.

18. A flow-through method for converting glycerol to butanol, the method comprising:
    providing a feedstock comprising glycerol;
    passing the feedstock through a reaction chamber containing a superparamagnetic catalyst, wherein the superparamagnetic catalyst comprises $Fe_2ZnO_4$; and
    exposing the feedstock to a fluctuating magnetic field within the reaction chamber to form a product comprising butanol.

* * * * *